Figure 1:
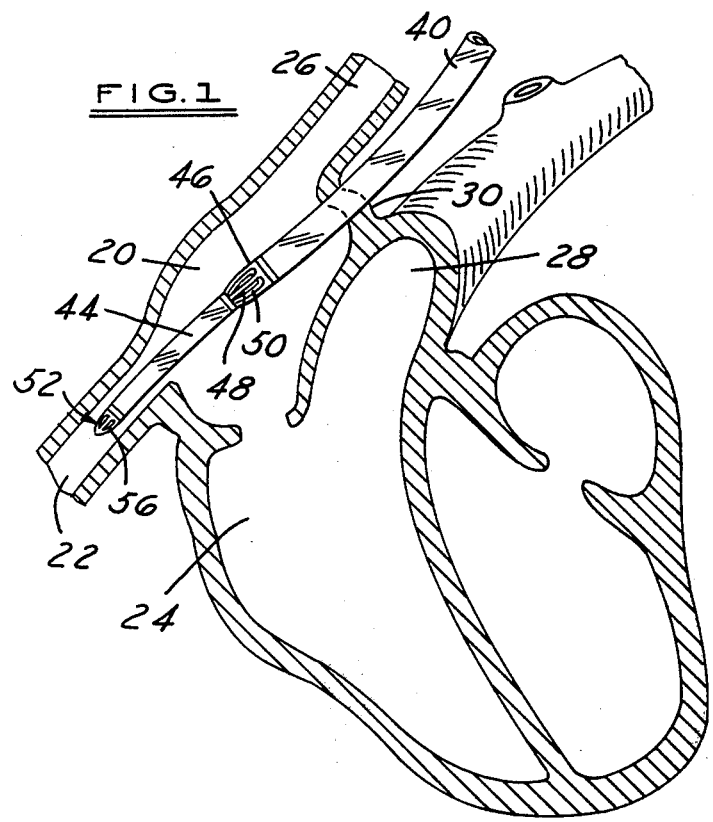

United States Patent [19]

Amrine

[11] 4,129,129
[45] Dec. 12, 1978

[54] VENOUS RETURN CATHETER AND A METHOD OF USING THE SAME

[75] Inventor: Bruce A. Amrine, Ann Arbor, Mich.

[73] Assignee: Sarns, Inc., Ann Arbor, Mich.

[21] Appl. No.: 779,018

[22] Filed: Mar. 18, 1977

[51] Int. Cl.² .................. A61M 1/03; A61M 25/00
[52] U.S. Cl. ................................. 128/214 R; 128/348
[58] Field of Search .......... 128/214 R, 214 Z, 214 B, 128/221, 347–351

[56] References Cited

U.S. PATENT DOCUMENTS

| 2,269,823 | 1/1942 | Kreiselman | 128/348 X |
| 3,851,646 | 12/1974 | Sarns | 128/214 R |
| 4,011,869 | 3/1977 | Seiler | 128/276 |

OTHER PUBLICATIONS

Maraist et al., "Experimental Cardiac Surgery" Surgery vol. 31, No. 1 Jan. 1952, pp. 146–153.
Sabiston-Textbook of Surgery-1972 (Davis-Christopher) pp. 2112–2113.

*Primary Examiner*—Dalton L. Truluck
*Attorney, Agent, or Firm*—Barnes, Kisselle, Raisch & Choate

[57] ABSTRACT

A method and device for connecting a life support machine to the heart of a patient during open heart surgery which includes a two-stage venous return catheter having spaced inlet openings in the tip end and spaced from the tip end to insure proper connection to the various cavities of the heart and adequate return flow for a life support machine.

7 Claims, 11 Drawing Figures

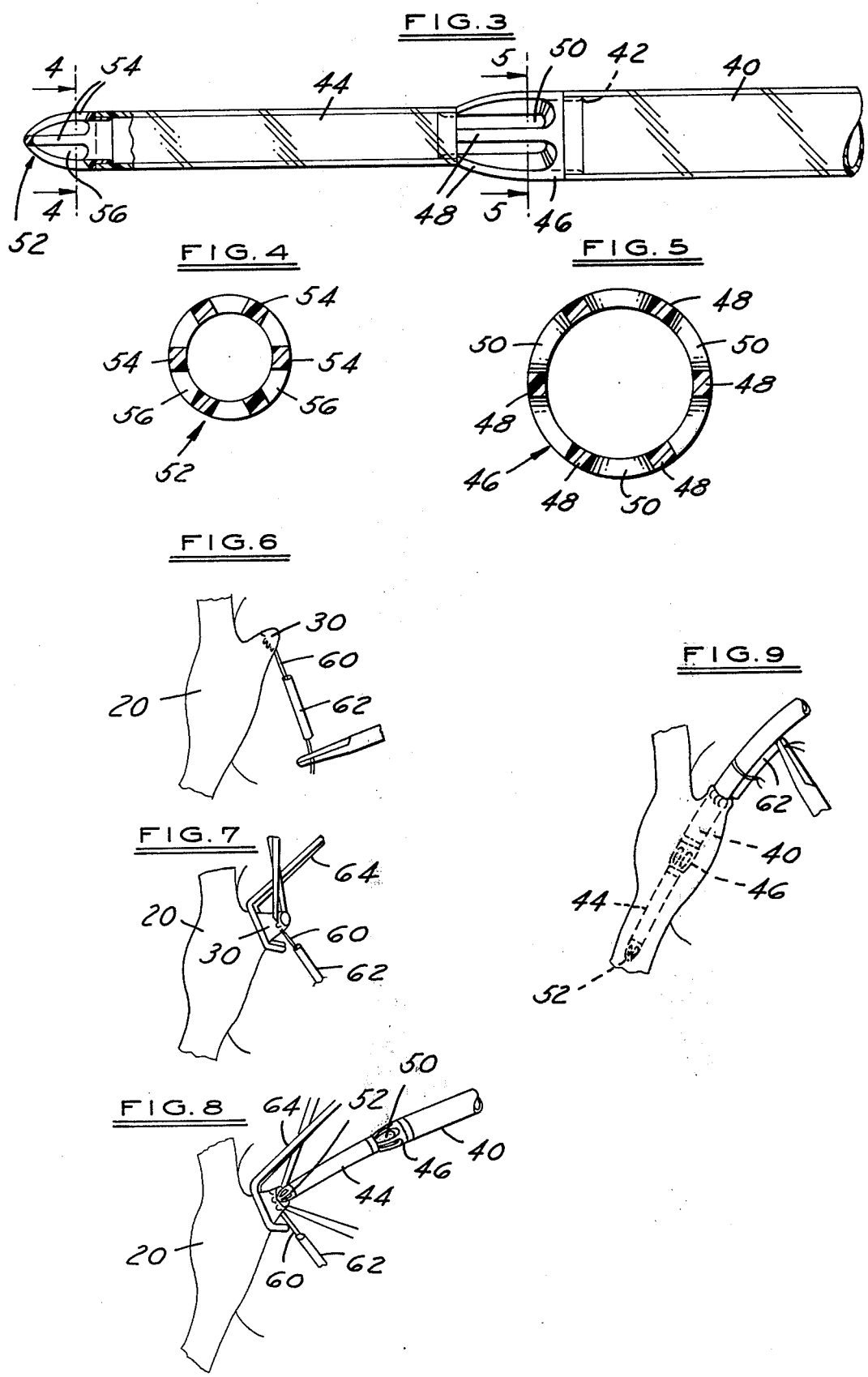

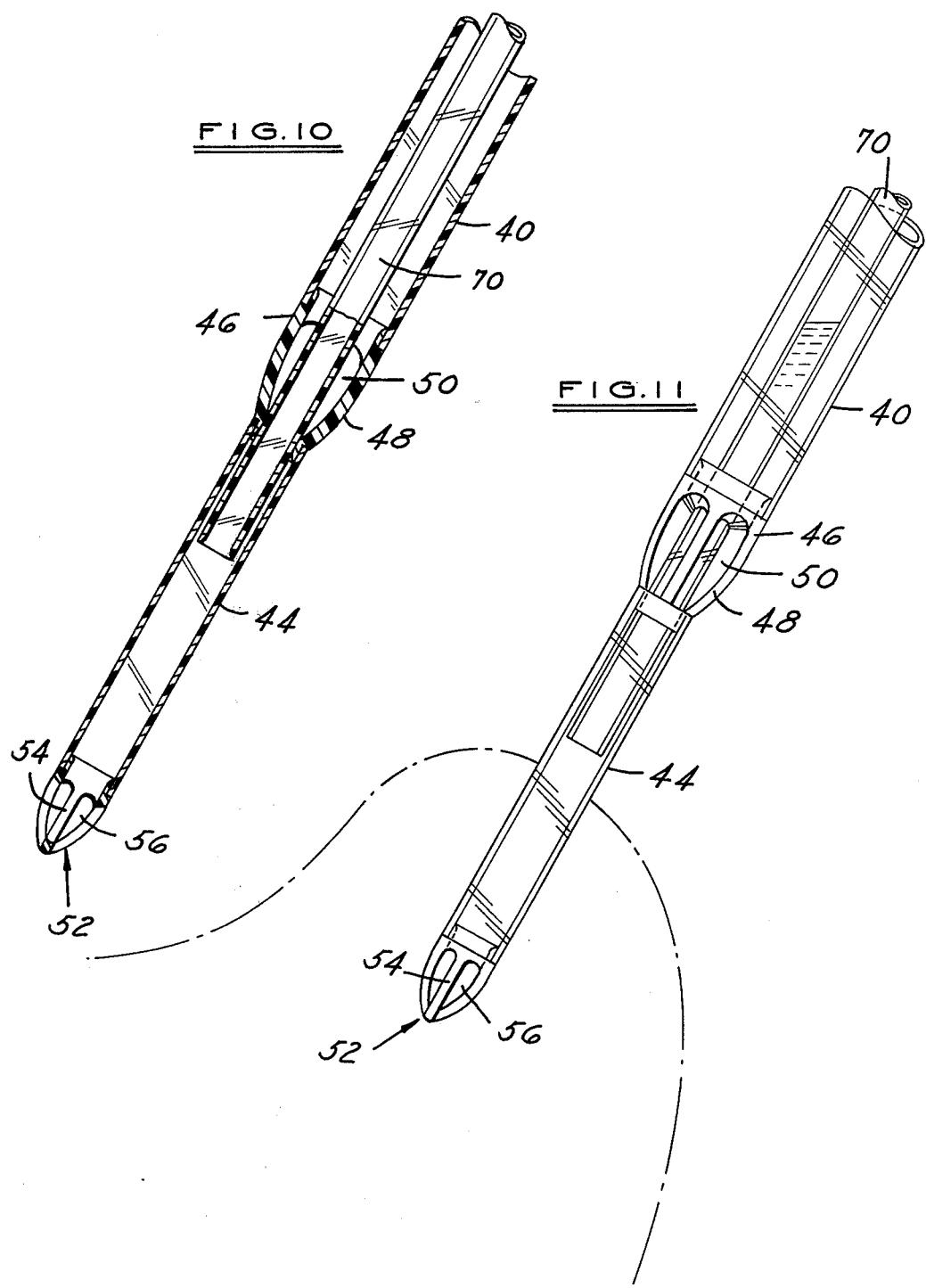

VENOUS RETURN CATHETER AND A METHOD OF USING THE SAME

This invention relates to a venous return catheter and a method of using the same, and more particularly to a catheter used with a life support machine during the course of open heart surgery.

In heart surgery, life support machines are utilized to perform temporarily the function of the heart and lungs while the patient's heart is being surgically serviced such as the repair of heart wall lesions, installation of a valve, and by-pass artery work. The life support machine must take the flowing blood from the patient, maintain the temperature pressure and flow rate within certain physiologic limits, and provide the lung function.

In the course of an operation of this type, it is essential that a change-over be accomplished from the natural heart function to the machine. This involves installation of a venous return catheter into the right atrium (chamber) of the heart to serve as a drainage supply connection to the pumping machine. Experience has shown that, when used in certain procedures such as coronary artery by-pass to the circumflex coronary artery, anatomical variations and intra-operative manipulation of the heart may cause a reduction in venous drainage due to distortion of the atrial walls and vena cava or shifting of the catheter position.

The traditional method of venous drainage has been to place two catheters, one into the superior vena cava. This method provides good venous return in all operative circumstances but requires that additional time be spent placing the two catheters. Single catheter venous drainage from the right atrium was developed to simplify and shorten the time required for cannulation. However, the disadvantage of single catheter drainage from the right atrium only is its limitation to those procedures not requiring the previously discussed operative manipulations which reduce the blood flow. The two-stage catheter to be described combines the desirable simplicity, convenience, and time savings of the single catheter with the higher reliability of the two catheter technique.

To alleviate this problem and insure a proper blood flow, a two-stage venous return catheter designed in accordance with the present invention is provided. This catheter has a small diameter pilot tip extending beyond the main catheter entrance area which assists in the maintenance of adequate venous drainage by collecting venous blood directly from the inferior vena cava while the larger reducing adapter collects the flow of blood from the superior vena cava and the coronary sinus.

It is thus an object of the invention to provide a venous catheter which is easily installed and which insures adequate drainage during a heart operation. It is a further object to provide a catheter designed for maximum flow and one which can be installed with a minimal loss of blood and through a single aperture created by the amputation or incision of a portion of the distal appendage.

Other objects and features of the invention will be apparent in the following description and claims in which there is set forth the invention together with details to enable a person to practice the invention, all in connection with the best mode presently contemplated for the invention.

Drawings accompany the disclosure and the various views thereof may be briefly described, as:

FIG. 1, a view of a sectioned human heart with the two-stage catheter in proper position.

Figure 2:
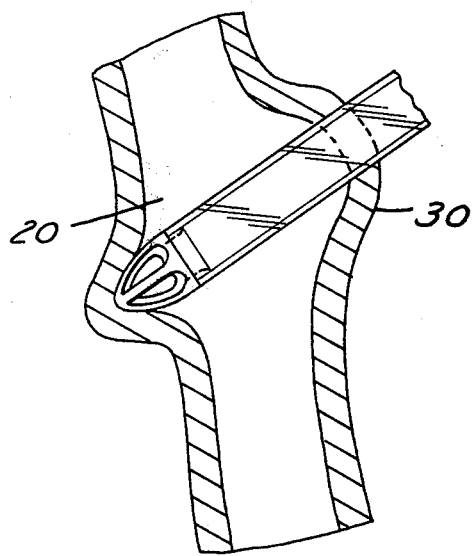

FIG. 2, a view of an improperly installed single stage catheter.

FIG. 3, is a side view, partially in section, of the two-stage catheter.

FIG. 4, a sectional view on line 4—4 of FIG. 3.

FIG. 5, a sectional view on line 5—5 of FIG. 3.

FIGS. 6, 7, 8 and 9, illustrations of the successive stages in the installation of the catheter.

FIG. 10, a view of the catheter with an installation obturator in place.

FIG. 11, a view showing the function of the obturator in initial installation.

With reference to the drawings, in FIG. 1, a section of a human heart is illustrated showing the right atrium 20 above the inferior vena cava 22, the right ventricle, and superior vena cava 26, and the pulmonary artery. The normally shaped right atrium has an atrial appendage 30 shown best in FIGS. 6 to 9. This is the usual location for the return catheter insertion as will be described.

In FIG. 3, the two-stage venous return catheter is illustrated having a main body tube 40 formed of a molded plastic tubular material such as, for example, polyvinylchloride joined in a heat sealed or solvent cemented telescoping joint 42 to a catheter body 44 having an enlarged reducer end 46 merging with the tubular body 40, this reducer end 46 tapering in a curved contour to the smaller or pilot body 44. The tapering reducer portion 46, shown in section in FIG. 5, has a plurality of circumferentially spaced ribs 48 which form six radial slots 50 extending longitudinally along the end 46. At the distal end of body 44 is an insertion nose or tip portion 52, which tapers from the diameter of flexible tube 44 to a rounded end, and which has circumferentially spaced ribs 54 which form six radial passages 56 ensmalling from the body 44 to the rounded end 52. The parts 40, 46, 44 and 52 can be made separately and telescoped together in sealed joints or they may be molded as one piece. A proper tubular connection (not shown) is provided for the flexible elongated (about 12 inches (30.5 cm)) tubular body 40 for the cooperation with the life support machine. The body 40 is 2 to 3 inches (5 to 7 cm) in length). The parts 46 and 52 are of relatively rigid plastic, such as polyvinylchloride, for example, while the tubular body 40 and body 44 preferably have flexing qualities.

The use of the catheter, a purse-string suture 60 is placed around the right atrial appendage 30 and drawn through a rubber ligature tube 62 (FIG. 6). A vascular clamp 64 (FIG. 7) is used to isolate the purse string while the end of the distal appendage 30 is amputated or incised within the purse string. The atriotomy is then opened with clamps or traction sutures and the tip 52 of the catheter is inserted (FIG. 8). The occluding vascular clamp is then released while the catheter is further inserted into the atrium toward the inferior vena cava 22. Both the tip 52 and the reducer 46 should be inserted smoothly and quickly to minimize blood loss through the reducer. The distal tip 52 is advanced into the inferior vena cava, thus positioning the reducer centrally in the right atrium 20 as shown in FIG. 1. This permits collection of blood from the coronary sinus and venous return from the superior vena cava 26. The clamps or traction sutures are then removed. The purse string suture 60 is then tightened around tube 40 and clamped and the ligature tube is tied to the catheter tube 40 (FIG. 9). When the operation is completed, the catheter is removed and the purse string suture tied.

In some instances, it may be desired to utilize an obturator tube to provide more time for catheter insertion and reduce blood loss. It will be recognized that after the tip 52 is inserted and before the reducer 46 is received within the atrium, some blood may escape through the reducer openings 50. This can be prevented by inserting an obturator tube 70 into the body 44 as shown in FIG. 10. This will conduct initial blood flow back into the tube 40 and temporarily block the openings 50 in the reducer 46 as shown in FIG. 11. Once the reducer 46 is installed in the atrium, the obturator tube 70 may be retracted to allow full flow through tip and reducer.

As illustrated in FIG. 2, a single stage catheter may become misdirected and the catheter openings occluded. This may occur when the surgeon relocates the tubing or when the heart is manipulated or rotated to gain exposure of an otherwise inaccessible area. Thus, blood flow may be blocked for periods which can cause dangerous conditions in life support. The two stage catheter insures further insertion which tends to prevent this occlusion and also provides ample flow in the atrium through the reducer portion 46. Thus, the risk of occlusion is much reduced if not totally eliminated.

I claim:

1. In a method of by-passing blood flow from the heart during open heart surgery, those steps which comprise:
   (a) introducing a venous return catheter into the right atrium of the heart and extending the catheter into the inferior vena cava,
   (b) providing first drainage openings in the catheter adjacent the end of the catheter in the inferior vena cava,
   (c) providing second drainage openings in the catheter spaced from the end to lie in the right atrium, and
   utilizing a single tube in the catheter to carry the blood flow from the inferior vena cava and the right atrium to extracorporeal life support equipment.

2. A method as defined in claim 1 in which a tubular obturator is inserted into said catheter to the first drainage openings to block the second drainage openings during initial insertion of the catheter, and removing the obturator after the second drainage openings have entered the right atrium.

3. In a method of by-passing blood flow from the heart during open heart surgery, those steps which comprise:
   (a) circumferentially suturing the right atrial appendage,
   (b) surgically entering the right atrial appendage,
   (c) releasing the suture and inserting a venous return catheter into the right atrium of the heart and extending the catheter into the inferior vena cava,
   (d) providing first drainage openings in the catheter adjacent the end of the catheter in the inferior vena cava,
   (e) providing second drainage openings in the catheter spaced from the end to lie in the right atrium, and
   (f) utilizing a single tube in the catheter to carry the blood flow from the inferior vena cava and the right to atrium to extracorporeal life support equipment.

4. A method as defined in claim 3 in which a tubular obturator is inserted into said catheter to the first drainage openings to block the second drainage openings during initial insertion of the catheter, and removing the obturator after the second drainage openings have entered the right atrium.

5. A two-stage venous return catheter for insertion into the right atrium and inferior vena cava of the heart to drain blood of the patient to an extracorporeal life support machine which comprises:
   (a) a first diameter tube having an insertion end portion,
   (b) a rounded nose portion on the insertion end of said tube having circumferentially spaced elongate slots on the sides to admit fluid,
   (c) an enlarged second diameter portion on said tube spaced from the end portion, and
   (d) a juncture between said first and second diameter portions having elongate slots to admit fluid into said enlarged portion.

6. A two-stage venous return catheter as defined in claim 5 in which said juncture portion tapers gradually from said first diameter portion to said second diameter portion.

7. A two-stage venous return catheter for insertion into the right atrium and inferior vena cava of the heart to drain blood of the patient to an extracorporeal life support machine which comprises:
   (a) a first diameter tube having an insertion end portion,
   (b) a rounded nose portion on the insertion end of said tube having circumferentially spaced elongate slots on the sides to admit fluid,
   (c) an enlarged second diameter portion on said tube spaced from the end portion,
   (d) a juncture between said first and second diameter portions having elongate slots to admit fluid into said enlarged portion, and
   (e) a removable obturator tube having a slip fit with the inner diameter of said first diameter tube to block flow through said slots in said juncture portion during insertion of said catheter into the atrium and inferior vena cava.

* * * * *